(12) United States Patent
Eriksson et al.

(10) Patent No.: US 6,821,339 B2
(45) Date of Patent: Nov. 23, 2004

(54) PROCESS FOR THE CRYSTALLIZATION OF NON-SUCROSE SUBSTANCES

(75) Inventors: Kristian Eriksson, Turku (FI); Juha Nurmi, Kirkkonummi (FI); Jouko Virtanen, Kantvik (FI)

(73) Assignee: Finnfeeds Finland Oy, Espoo (FI)

( * ) Notice: Subject to any disclaimer, the term of this patent is extended or adjusted under 35 U.S.C. 154(b) by 5 days.

(21) Appl. No.: 10/181,280

(22) PCT Filed: Jan. 16, 2001

(86) PCT No.: PCT/FI01/00036

§ 371 (c)(1),
(2), (4) Date: Nov. 18, 2002

(87) PCT Pub. No.: WO01/56956

PCT Pub. Date: Aug. 9, 2001

(65) Prior Publication Data

US 2003/0131784 A1 Jul. 17, 2003

(30) Foreign Application Priority Data

Jan. 31, 2000 (FI) .............................. 20000197

(51) Int. Cl.⁷ ................................................ C30B 7/14
(52) U.S. Cl. ............................ 117/68; 117/69; 117/70; 117/925; 117/926; 422/245.1; 23/293 R
(58) Field of Search .......................... 117/68, 925, 926, 117/69, 70; 422/245.1; 23/293 R

(56) References Cited

U.S. PATENT DOCUMENTS 4,359,430 A  11/1982  Heikkila et al.
4,476,248 A  * 10/1984  Gordon et al. .............. 562/494
4,504,457 A  *  3/1985  Saeman ...................... 423/474
6,086,681 A   7/2000  Lindroos et al.

FOREIGN PATENT DOCUMENTS

| DE | 18 11 870 | 8/1970 |
|---|---|---|
| DE | 195 35 017 | 11/1996 |
| FI | 3336/70 | 6/1971 |
| FI | 101980 | 9/1998 |
| FR | 2024559 | 8/1970 |
| SU | 798565 | 1/1981 |
| SU | 425420 | 8/1982 |
| WO | WO 96/27029 | 9/1996 |

OTHER PUBLICATIONS

Mathlouthi, M. et al. "Sucrose, Properties and Applications", Blackie Academic Professional, Suffolk, Great Britain, 1995, p. 49–64.
Madsen, R.F., "Vacuum pan automation and sugar house computer control", Paper presented at the 23$^{rd}$ Tech. Conf. British Sugar Corp., 1976.

* cited by examiner

Primary Examiner—Robert Kunemund
(74) Attorney, Agent, or Firm—Scully, Scott, Murphy & Presser

(57) ABSTRACT

The invention relates to a process for the crystallization of substances having a narrow metastable supersaturation zone. In the process the saturation of a solution is gradually increased and the solution is seeded for the crystallization. The seeding is performed at a seeding point which is selected in response to a signal received from said process indicating imminent or initial spontaneous nucleation. The process provides a good crystal yield and a crystalline product having a uniform crystal structure and a narrow crystal size distribution.

19 Claims, No Drawings

PROCESS FOR THE CRYSTALLIZATION OF NON-SUCROSE SUBSTANCES

The present invention relates to a process for the crystallization of substances having a narrow metastable supersaturation zone. The invention especially relates to a controlled crystallization of such compounds so as to provide a good crystal yield and a crystalline product having a uniform crystal structure and a narrow crystal size distribution.

The invention is useful for controlling the crystallization of substances for which hitherto no clear model for the crystallization is known and which hence are often crystallized in a very uncontrolled way. The invention is especially adapted to the crystallization of compounds with a narrow metastable supersaturation zone, such as betaine, potassium chloride, ammonium chloride, and the like.

Common sugar or sucrose is one of the most commonly crystallized compounds in industry and an enormous amount of work has been put into developing models and automation techniques for the crystallization of sucrose. It is well known in the art that there is a large number of parameters which influence the crystallization processes either separately or in intertwined combinations with each other.

The two principal steps of crystallization are the formation of crystal seeds (nucleation) and crystal growth. In most industrial processes crystallization is primarily based on crystal growth. The state of the art with respect to crystallization is represented, for instance, by Mathlouthi, M. and Reiser, P. (ed), Sucrose, Properties and Applications, Blackie Academic Professional, Suffolk, Great Britain, 1995, p.49 ff. This document explains the crystallization mechanism with respect to both nucleation and crystal growth. With respect to the industrial crystallization of sucrose the document states, for instance, that one must avoid concentrating the solution up to the nucleation zone, i.e. the zone whereat spontaneous nuclei formation readily occurs (p. 58); one must avoid the creation of an uncontrolled number of seeds (p. 59); and the crystallization should be carried out in the metastable zone not too close to the nucleation zone and the saturation curve (p. 60 to 61 and 63 to 64).

The metastable zone is the zone where spontaneous crystal formation will occur in the solution only if crystals are already present. The crystallization of sucrose is thus advantageously performed well within the metastable zone. Since sucrose, like most organic compounds, especially carbohydrates, is a compound which has a fairly broad metastable zone, this allows the crystallizer to monitor the supersaturation for selecting a suitable seeding point within said zone and for controlling the progress of the crystallization also within said zone.

A process for crystallizing organic compounds from their solutions having a high viscosity and supersaturation by spontaneous or active seeding and subsequent cooling is described in the same applicant's WO publication 9627029. Said invention aims at providing crystallization without any significant crystal growth.

Seeding of the solution is normally utilized in crystallization since the seeds introduced into the solution provide nucleation centers around which the actual crystal growth primarily occurs. Providing a multitude of seeds into the solution will minimize spontaneous nucleation and will result in a high crystal yield with a uniform structure and a narrow crystal size distribution.

Seeding of sucrose solutions forms one part of the common control techniques used in sucrose crystallization. Publications describing techniques for the seeding of sucrose solutions are, for instance, Madsen, R. F., Vacuum pan automation and sugar house computer control, Paper presented at the 23rd Tech. Conf., British Sugar Corp., 1976, which describes means for measuring whether the massecuite in a pan has the right conditions for seeding. Such means comprise measuring the electrical conductivity, the rheology or the refractive index;

DE 19535017, which describes cooling of a sucrose solution until a supersaturation of 1.2 to 1.3 has been obtained and subsequent introduction of air bubbles into said sucrose solution;

SU 798565 describes monitoring spontaneous crystal formation in a separate cooled circulation tube and seeding a sucrose solution within the metastable zone in response to a difference observed in the light passing through said tube and a reference tube. The crystal formation in the cooled tube starts between 3 and 10 minutes before any spontaneous nucleation occurs in the actual crystallizer.

In the prior art very few descriptions are found on how to control the seeding of other compounds than sucrose, i.e. non-sucrose compounds. Although some non-sucrose compounds may mimic sucrose in their nucleation and crystallization behaviour, it is evident that some others will behave very differently. It is not clear to those skilled in the art how a non-sucrose compound crystallization should be controlled.

The techniques for seeding sucrose solutions naturally take into account the need to seed the solution well within the rather broad metastable zone. For compounds with a narrow metastable zone the seeding and the subsequent crystallization is much more difficult to control since in most cases the measurements indicating that the saturation has reached the metastable zone are not exact enough for allowing time to seed before excess spontaneous seeding has taken place. The solution can be analyzed and monitored for parameters such as purity, concentration, density, viscosity, conductivity, boiling point elevation, refractometric index, etc. These parameters will indicate when the solution is getting close to saturation and thus close to the correct seeding point. However, for compounds with a narrow metastable zone monitoring these well known parameters has not been found to give an exact enough information for allowing prediction of the correct seeding point. In many cases the calibration accuracy of the instruments is not exact enough and the crystallization parameters vary from batch to batch so that predetermination of the seeding point based on these measurements is difficult if not impossible. Proper seeding in such cases requires extreme skills and apparatus-bound experience by the operator.

The result of an incorrect seeding is that the crystals obtained will most likely be non-uniform in structure and may have a wide crystal size distribution making the efficient separation of the crystals from the mother liquid difficult. An uneven size distribution also provides a product with poor final crystal quality. The crystal size distribution affects product parameters such as the free-flowing properties, hygroscopicity, bulk density, etc.

The present invention strives to overcome the problem of crystallization control of substances having a narrow metastable zone.

The present invention provides a means for controlling the seeding of non-sucrose compounds. It is especially adapted for controlling the seeding of non-sucrose compounds having a very narrow metastable supersaturation zone.

The present invention is defined in the appended claims, which are incorporated as such into the present specification. The present invention relates to a process for the crystallization of a substance having a narrow metastable supersaturation zone, wherein the saturation of a solution of said substance is gradually increased and said solution is seeded for the crystallization. The invention is characterized in that seeding is performed at a seeding point which is selected in response to a signal received from said process indicating imminent or initial spontaneous nucleation, said seeding initiating a controlled crystallization based on crystal growth around the nuclei provided by said seeding and enabling the production of a crystalline product having a uniform crystal structure and a narrow crystal size distribution.

The crystallization after seeding may be monitored in a conventional way or may be subjected to specific conditions required by the substance to be crystallized. Such crystallization conditions will be readily selected by those skilled in the art and they form no part of the present invention.

In the present description and claims the term "narrow metastable zone" means that the zone in which the solution can exist in saturated condition without spontaneous nucleation or crystal formation occurring is very narrow. The substance to be crystallized according to the present invention thus is one that crystallizes in the crystallization conditions of said process at a supersaturation which is 1.0 or close to 1.0, where the supersaturation (s) is calculated as $$s=[Q*x/(100-x)]/[Q*L/(100-L)];$$
$$s=x/(100-x)*(100-L)/L$$

where
Q=purity of said solution as % of the dry matter
x=dry matter content of the mother liquid, given as mass % of the total weight
L=solubility given as mass % at the purity Q.

Examples of such compounds are salts such as potassium chloride and ammonium chloride, betaine in anhydrous or monohydrate form, betaine hydrochloride etc. The preferred non-sucrose compound of the invention with a narrow metastable supersaturation area is betaine.

Crystallization of betaine has been described in the prior art in U.S. Pat. No. 4,359,430 and in the above mentioned WO publication 9627029. Seeding of betaine solutions has traditionally been performed by operators who have acquired the experience by empirical trials and who, consequently, have learned to know their own crystallizing equipment.

The term "seeding point" of the present invention indicates a point in time at which active seeding of the solution is performed.

The term "controlled crystallization" is used to indicate that the crystallization proceeds along reproducible and predictable lines under normal monitoring of crystallization parameters such as temperature, liquid feed, vacuum, etc.

As a result of the present invention, the crystals in the solution will start to grow under uniform crystallization conditions and will consequently have a "uniform crystal structure". This means that, for instance, where there exists a possibility of the production of different crystal forms of the same substance, the crystals produced according to the present invention will predominantly be of the same crystal form. Since the crystals will grow around the seeding-induced nuclei, the resulting product will also have a narrow crystal size distribution, which is important i.a. for proper recovery of the crystals and for providing a uniform crystal product having good free-flowing properties.

The term "narrow crystal size distribution" should be taken to mean that the product, on an average and after removal of any fines and oversized lumps, has a large proportion of the crystals within a narrow range. Crystal size distribution is a parameter which is much used for indicating the quality of a crystal yield. It is determined from the results of a sieve test by means of standard methods. The most commonly used calculation method is the so called Powers method which has been adopted by ICUMSA (International Commission for Unifrom Methods of Sugar Analysis). The average crystal size and the Coefficient of Variation (CV) are calculated from the cumulative weight percentages of the size fractions. The CV is calculated from the arithmetic mean of the two apertures matching the cumulative percentages 84% and 16% and divided by the aperture at 50%:

$$CV=100\times(a16\%-a84\%)/2/a50\%$$

where "a" indicates the aperture at the specified value.

The seeding may be performed by introduction of a slurry, a powder, air bubbles, ultra sound, etc. The seeds may be of the same crystalline material as the product, or the seeding may be performed by other means, which are well known as such.

In a preferred embodiment of the present invention the controlled crystallization initiated by the seeding provides crystals having a crystal size which, on an average, is larger than 0.25 mm, preferably between 0.35 and 1.0 mm.

In the operation of the present invention the maturing of the solution is monitored so that the exact and critical point at which seeding should take place can be correctly detected. Consequently, the solution is monitored for detecting a signal which indicates that the solution is mature for seeding, i.e. that the saturation is entering the metastable zone. Since the substance has a very narrow metastable zone, the seeding point is so critical that normal means for measuring the supersaturation as used for sucrose is generally speaking not sensitive enough. Normal monitoring parameters for the supersaturation may of course be used to indicate that the solution is getting near to the seeding point. Such parameters may be selected from density, viscosity, consistency, conductivity, refractometric index, boiling point elevation, etc. When attempts are made to run the seeding only based on these traditional means, the seeding will very likely be unsuccessful, the seeds will dissolve or spontaneous seeding will have taken place. The result is that the crystallization proceeds as if no seeding had been made.

According to the invention, the signal which indicates maturity of the solution i.e. that spontaneous nucleation is imminent or has just been initiated may be detected by optical, acoustic, chemical, physical, physico, chemical, and/or electric means.

The signal is preferably detected optically by visual means as an observation of the first spontaneous nucleation in the solution and the seeding is performed immediately in response to this signal.

The visual observation may be made with a microscope. However, it is also possible to register it automatically by a photocell or another instrument capable of detecting solid particles in a solution.

The signal may advantageously be detected in a portion of the solution which is subjected to different physical conditions than the main part of said solution. Thus, a portion of the solution may be conducted through a pipe with a visual observation means and or a means for detecting minute crystals by filtering or other physical means.

The signal may also be detected acoustically as a change in the sound or other vibrations emanating from a crystallizing equipment when spontaneous nucleation is imminent and/or initiated. The sound may be amplified and/or it may be detected with a stethoscope and registered by a computer capable of sensing small changes in the sound.

In specific situations, especially where the purity of the substance in the solution is very high, above 95% or more, preferably between 98 and 100%, it has been found that the signal may be detected as a change in the temperature gradient of said solution. This surprising feature is especially clear in the case of anhydrous betaine having a very high purity.

The substance to be seeded and crystallized according to the present invention is preferably betaine, a salt or derivative thereof, an inorganic salt, or the like crystallizable compound having a narrow metastable supersaturation zone.

Typical substances are betaine, betaine hydrochloride potassium chloride or ammonium chloride.

The preferred crystalline products are anhydrous betaine and betaine monohydrate, the solutions of which are seeded with crystals of anhydrous betaine or betaine monohydrate.

The average crystal size of anhydrous betaine is preferably between 0.4 and 0.5 mm, while the average size of the betaine monohydrate generally is slightly larger, between 0.4 and 0.7 mm, after the normal removal of fines and oversized lumps.

The size distribution of the crystal yield depends on the average size of the crystals and no absolute numerical values can therefore be given. However, the Coefficient of Variation (CV) for a narrow size distribution is generally below 40% and preferably below 30%. For crystals having an average size of 0.4 to 0.5 mm a size distribution as low as 25% (CV) can be obtained with seeding according to the present invention. In a poor particle size distribution the CV is above 40% and may even be well above 50%.

The crystallization process of the present invention may be an evaporative crystallization or a cooling crystallization. It is preferably a batch process, but the present invention can advantageously be used in the start up of a continuous crystallization.

The seeding point of the present invention is preferably selected so as to provide seeding immediately after the first spontaneous crystallization has been detected. However, when the imminent spontaneous nucleation is detected e.g. by a change in the temperature gradient of the solution or by nucleation in a separate portion of the solution, there may be a set interval between the said signal and the seeding point.

In an evaporation crystallization process according to the present invention an undersaturated solution of the non-sucrose compound which is to be crystallized is fed into a vacuum pan to reach a predetermined level, which is generally defined by the height required to cover the heat exchange element of the pan.

In a typical boiling sequence the level in the pan rises from zero to a set point while the density generally at this stage corresponds to the undersaturation conditions of the feed solution.

When vacuum and heat are applied to the pan the solvent water of the undersaturated solution evaporates and the density of the solution increases with time while the level in the pan is generally maintained at said set level by additional feed of undersaturated solution. The concentration of the solution continues to increase towards saturation. When the concentration reaches a set value close to saturation the feed of liquor is preferably stopped and the solution is monitored for the signal indicating that seeding should be performed.

The solution may be transferred to a cooling crystallizer for a cooling crystallization either before or after seeding.

When the signal has been detected the batch is seeded. Thereafter the batch is ready for the start of the boiling up or cooling and a continued controlled crystallization.

According to a preferred embodiment of the present invention seeding of the solution is performed just after the first spontaneous crystal formation in the solution has been detected. Preferably seeding is performed by adding a slurry or powder of small crystals immediately after spontaneous crystallization has been observed. A visual observation by microscope is often the best but there are also means for automation of the observation, as will be described.

The boiling up or cooling generally starts substantially immediately after the seeding although there may in some cases be a predetermined time span between the seeding and the start of said actual crystallization stage.

The saturation conditions during the crystallization should be monitored to allow an optimal growth of the crystals only around the nuclei created at the seeding. When the crystals have grown to their final size, the boiling or cooling is ready, the crystallizer is emptied.

Since crystallization takes place only above a certain saturation level, some of the compound remains in the mother liquor and it is thus preferred to repeat the crystallization process for the mother liquor in one or more strikes.

The present invention is especially well adapted to accounting for the crystallization in several strikes, wherein the amount of impurities in the syrup increases from strike to strike. Despite the increasing impurity of the solution the correct seeding point will be detected according to the invention and the result will always be a product of a better quality than the product obtainable without using the present invention.

The invention will now be illustrated with reference to some working examples.

EXAMPLE 1

Manual Seeding of a Betaine Boiling Batch

Evaporation Crystallization, Technical Quality

The crystallization was carried out with a betaine feed liquor of technical quality, purity 89% betaine/ds. The process started with juice intake until covering the calandria. The concentration of the solution was increased while additional liquor was fed into the pan. The concentrating continued with a constant feed of steam at a vacuum of −0.77 bar (−78 kPa) until the refractometer showed that saturation was close. The feed of liquor was stopped. The operator started looking for changes in the solution through a microscope applied to the side glass of the pan. When the first spontaneous crystals were observed, the pan was immediately seeded with a slurry containing finely ground seed crystals. The temperature of the solution was 98.8° C. and the dry matter content was 77.7% (w/w).

After seeding the juice inlet started again for boiling up to full pan, 30 m$^3$. The final massecuite was discharged and centrifuged. The crystals were dried, cooled, sieved to remove lumps and finally packed.

The crystal size of the betaine anhydrous product was determined by sieving. The average size of the crystals was 0.45 mm, the crystal size distribution was 25% (CV).

EXAMPLE 2

Automatic Seeding of a Betaine Boiling Batch by Refractometer

Evaporation Crystallization, Pure Betaine

The crystallization was carried out with a betaine feed liquor of high purity, >99% betaine/ds. The process described in Example 1 was repeated several times with a different feed liquor using the same pan and with the same instruments while keeping the feed of liquor and steam at the same level and the vacuum at −0.78 bar (−79 kPa). The refractive index of the pure betaine solution was continuously monitored and the value at the appearance of the first spontaneous crystals was found to be 75.8% Brix in all cases. This value was taken as a set value for the pan.

The subsequent boiling started as previously with juice intake until covering the calandria. The concentration of the solution was increased while continuously and automatically monitoring the refractometric index by a refractometer connected to a computer. The concentrating continued with a constant feed of steam at a vacuum of −0.78 bar (−79 kPa). When the refractometer value reached close to the set value, the feed of liquor was stopped. When the set value of 75.8% Brix was reached the pan was automatically seeded with a slurry of finely ground seed crystals. The temperature was 97.2° C.

The boiling up to full pan was then continued as described in Example 1 and the final massecuite was discharged and centrifuged. The crystals were dried, cooled, sieved for removal on fines and lumps and finally packed.

The crystal size of the betaine anhydrous product was 0.42 mm, crystal size distribution 26% (CV).

EXAMPLE 3
Automatic Seeding of a Betaine Boiling Batch by Temperature

Evaporation Crystallization, Pure Betaine

The crystallization was carried out with a betaine feed liquor of high purity, >99% betaine/ds.

The process described in Example 1 was repeated several times in different pans and with slightly varying feeds of liquor and steam. The vacuum was kept at −0.78 bar (−79 kPa). The temperature of the pure betaine solution was continuously monitored while the concentration of the solution increased until the appearance of the first spontaneous crystals. The temperature was repeatedly and reproducibly found to stop rising at 97.2° C. just before the first spontaneous crystal formation was detected in the microscope. This change in the temperature gradient was found to indicate imminent spontaneous nucleation and was taken as a set value for the vacuum in question.

The subsequent boiling started as previously with juice intake until covering the calandria. The concentration of the solution was increased while continuously and automatically monitoring the temperature by a thermometer connected to a computer. The concentrating continued with a constant feed of steam at a vacuum of −0.78 bar (−79 kPa). The feed of liquor was continued even when the thermometer reading reached close to the set value. When the temperature stopped rising at 97.2° C. the pan was automatically seeded after a delay of 60 seconds.

The boiling up to full pan was then continued as described in Example 1 and the final massecuite was discharged and centrifuged. The crystals were dried, cooled, sieved for removal on fines and lumps and finally packed.

The crystal size of the betaine anhydrous product was 0.43 mm, crystal size distribution 26% (CV):

EXAMPLE 4
Manual Seeding of a Betaine Boiling Batch

Cooling Crystallization, Technical Quality

The crystallization was carried out with a betaine feed liquor of technical quality, purity 88% betaine/ds. The process started in a pan with juice intake until covering the calandria. The solution was then concentrated by evaporation under continuous juice intake until full pan, 30 m$^3$. At a concentration of 75.1% (w/w), the liquid was discharged into a cooling crystallizer at a temperature of about 93° C.

The cooling started and the operator begun looking for changes in the solution through a microscope at a side glass of the crystallizer. When the first spontaneous crystals were observed, the crystallizer was immediately seeded with a slurry of seed crystals. The temperature was 82.3° C.

After seeding the massecuite was cooled to an optimal crystal content for centrifugation. The final massecuite was discharged and centrifuged. The crystals were dried, cooled, sieved and finally packed. The crystal size of the betaine monohydrate product was 0.5 mm, the crystal size distribution was 32% (CV).

EXAMPLE 5
Automatic Seeding of a Potassium Chloride Boiling Batch by Temperature Evaporation Crystallization, Pure Potassium Chloride The crystallization is carried out with a potassium chloride feed liquor of 100% purity. The solution is continuously fed into a batch evaporation pan while keeping the level constant covering the calandria and increasing the concentration of the solution at a temperature of about 80° C. The temperature of the solution is kept at a constant value by regulating the vacuum.

The concentration of the solution is monitored by a refractometer and when the concentration has risen close to the saturation value the feed of liquor is stopped and the steam and vacuum are maintained at constant values. The temperature starts to rise and when the temperature profile shows a change the solution is seeded after 30 seconds with a slurry of finely ground potassium chloride crystals. The supersaturation at the seeding point is 1.00 and the concentration is 33.9% by weight.

After seeding the juice inlet starts again for boiling up to full pan, 30 m$^3$ in order to raise the level of the pan and increase the crystal size. The final massecuite reaches a concentration of 65% on dry substance and the mass is discharged and centrifuged. The crystals are dried, cooled and sieved. The crystal yield is 72% of good even sized potassium chloride crystals.

EXAMPLE 6
Manual Seeding of a Ammonium Chloride Boiling Batch

Cooling Crystallization, Technical Quality

The crystallization is carried out with an aqueous ammonium chloride feed liquor of technical quality, purity 95% NH$_4$Cl/ds. The process starts with juice intake until covering the calandria. Then the evaporation starts in order to increase the concentration of the solution at an underpressure and a temperature of about 85° C. The concentrating and juice intake continues until full pan, 30 m$^3$. At a concentration of 40.8% by weight, the liquid is discharged into a batch cooling crystallizer at a temperature of 85° C.

The solution is cooled at a temperature gradient of about 2° C. to 3° C. A portion of the solution is continuously circulated through a circulation line cooled to a temperature of 0.05° C. lower than the main body of the crystallizer. A photocell and a light source are connected to a transparent portion of the line. When the photocell registers the formation of the first spontaneous crystals in the circulation line, a red lamp is lighted and the operator starts to carefully monitor the solution through a microscope. Immediately when the first spontaneous nucleation is detected in the main body of the solution, the crystallizer is seeded with a slurry of finely ground NH$_4$Cl crystals. The temperature at seeding is 85° C. and the supersaturation is 1.00.

After seeding the massecuite is cooled to 20° C. providing an optimal crystal content for centrifugation. The final massecuite is discharged and centrifuged. The crystal yield of 33% is dried, cooled, sieved and finally packed. The average crystal size of the ammonium chloride product is 0.8 mm.

What is claimed is:

1. A process for the crystallization of a substance having a narrow metastable supersaturation zone, wherein the saturation of a solution of said substance is gradually increased and said solution is seeded for the crystallization, characterized in that seeding is performed at a seeding point which is selected in response to a signal received from said process indicating imminent or initial spontaneous nucleation, said seeding initiating a controlled crystallization based on crystal growth around the nuclei provided by said seeding and enabling the production of a crystalline product having a uniform crystal structure and a narrow crystal size distribution.

2. A process according to claim 1, wherein said crystal size is on an average>0.25 mm, preferably 0.35 to 1.0 mm, most preferably about 0.4 to 0.5 mm.

3. A process according to claim 1 or 2, wherein said signal is detected by optical, acoustic, chemical, physical, physicochemical, and/or electric means.

4. A process according to claim 3, wherein said signal is detected optically by visual means as an observation of the first spontaneous nucleation in said solution.

5. A process according to claim 4, wherein said visual observation is made with a microscope, or is registered by a photocell or another instrument capable of detecting solid particles in a solution.

6. A process according to claim 3, wherein said signal is detected acoustically as a change in the sound or other vibrations emanating from a crystallizing equipment when spontaneous nucleation is imminent and/or initiated.

7. A process according to claim 3, wherein said signal is detected as a change in the temperature gradient of said solution.

8. A process according to claim 1 or 2, wherein said substance is betaine, a salt or derivative thereof, an inorganic salt, or the like crystallizable compound having a narrow metastable supersaturation zone.

9. A process according to claim 8, wherein said substance is betaine, betaine hydrochloride, potassium chloride or ammonium chloride.

10. A process according to claim 9, wherein said substance is betaine.

11. A process according to claim 10, wherein said crystalline product is anhydrous betaine or betaine monohydrate.

12. A process according to claim 11, wherein said solution is seeded with crystals of anhydrous betaine or betaine monohydrate.

13. A process according to claim 7, wherein said solution comprises essentially pure betaine.

14. A process according to claim 13, wherein said betaine is crystallized as pure anhydrous betaine having a betaine purity of 99% on the dry substance, or more.

15. A process according to claim 1 or 2, wherein said signal is detected in a portion of said solution which is subjected to different physical conditions than the main part of said solution.

16. A process according to claim 1 or 2, wherein said crystallization comprises an evaporative crystallization or a cooling crystallization.

17. A process according to claim 16, wherein said crystallization comprises a batch crystallization or the start up of a continuous crystallization.

18. A process according to claim 1 or 2, wherein said seeding point is selected so as to provide seeding immediately after the first spontaneous crystallization has been detected.

19. A process according to claim 1 or 2, wherein a set interval is provided between said signal and said seeding point.

* * * * *